United States Patent [19]
Matsumoto et al.

[11] Patent Number: 6,134,503
[45] Date of Patent: *Oct. 17, 2000

[54] DATA PROCESSING UNIT FOR AND METHOD OF CHROMATOGRAPHY

[75] Inventors: Hirokazu Matsumoto, Shiga; Akihiro Adachi, Kyoto, both of Japan

[73] Assignee: Shimadzu Corporation, Kyoto, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/937,824

[22] Filed: Sep. 25, 1997

[30] Foreign Application Priority Data

Sep. 26, 1996 [JP] Japan ..................................... 8-277308

[51] Int. Cl.$^7$ ................................................. G01N 30/00
[52] U.S. Cl. ................................ 702/23; 702/22; 702/30; 702/32; 73/19.02; 73/23.36
[58] Field of Search .................................. 702/22–25, 27, 702/28, 30–32, 66–68, 70, 71, 73, 76, 183, 193, FOR 115–119; 73/19.02, 61.52, 61.53, 23.22, 23.26, 23.41, 23.42, 23.4, 23.35, 23.36, 23.37–23.39; 422/70, 80, 89, 94, 98, 83, 62, 68.1; 210/656, 198.2, 198.3, 657–659; 436/161, 162

[56] References Cited

U.S. PATENT DOCUMENTS

| | | | |
|---|---|---|---|
| 5,398,539 | 3/1995 | Gordon et al. | 73/19.02 |
| 5,436,166 | 7/1995 | Ito et al. | 422/89 |
| 5,610,835 | 3/1997 | Dominguez et al. | 73/19.02 |
| 5,827,946 | 10/1998 | Klee et al. | 73/23.36 |

*Primary Examiner*—Hal Wachsman
*Attorney, Agent, or Firm*—Majestic, Parsons, Siebert & Hsue P.C.

[57] ABSTRACT

For identifying components in a chromatographically analyzed sample, a chromatogram is produced and identification tables corresponding to presences and absences of specified components are preliminarily stored. Peaks corresponding to the specified components in the chromatogram are identified, and presences and absences of these specified components in the sample are thereby determined. A specified one of the identification tables is automatically selected according to the result of this determination of presences and absences, and components corresponding to individual peaks in the chromatogram are identified by using the selected identification table.

18 Claims, 4 Drawing Sheets

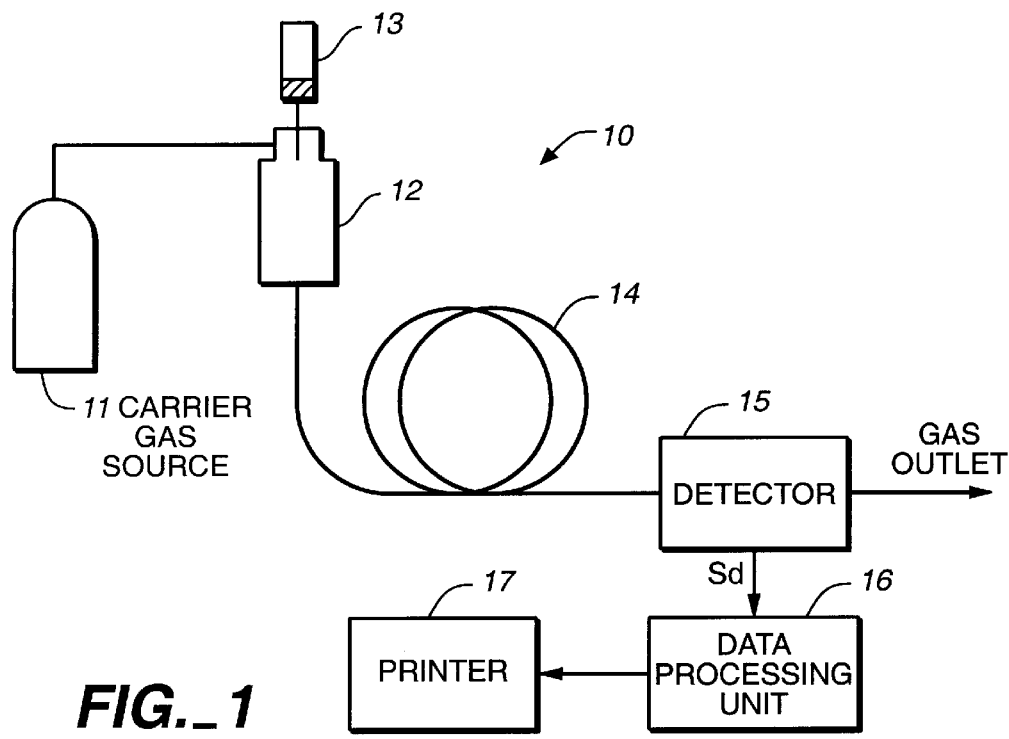
FIG._1
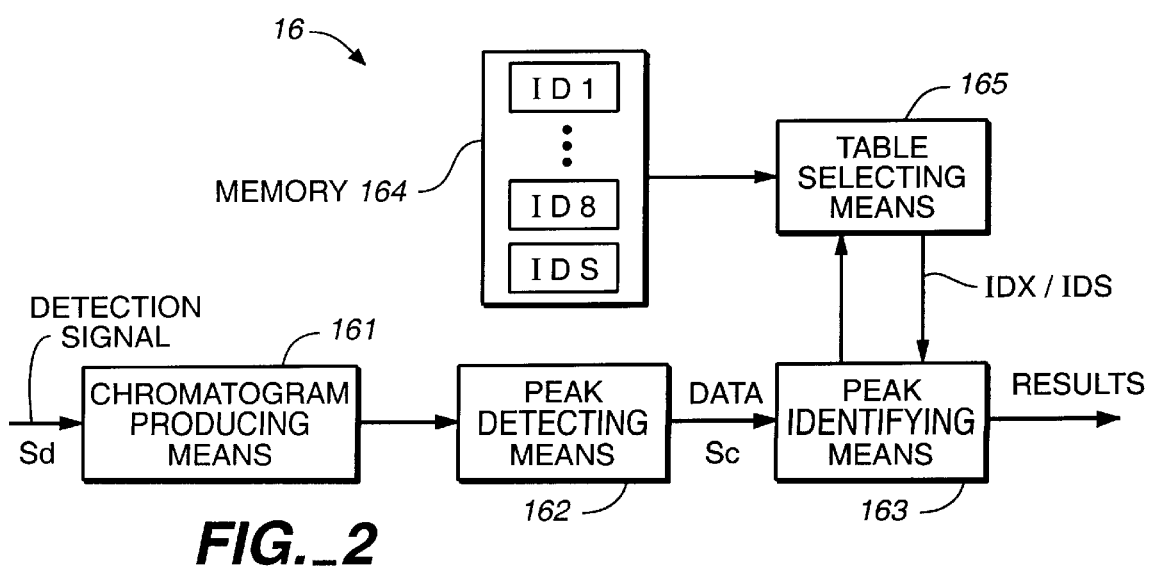
FIG._2

| COMPONENT | RETENTION TIME (MIN.) | WIDTH OF DETECTION WINDOW (MIN.) |
|---|---|---|
| a | 10 | ±1 |
| b | 12 | ±1 |
| c | 14 | ±1 |
| ⋮ | ⋮ | ⋮ |
FIG._3
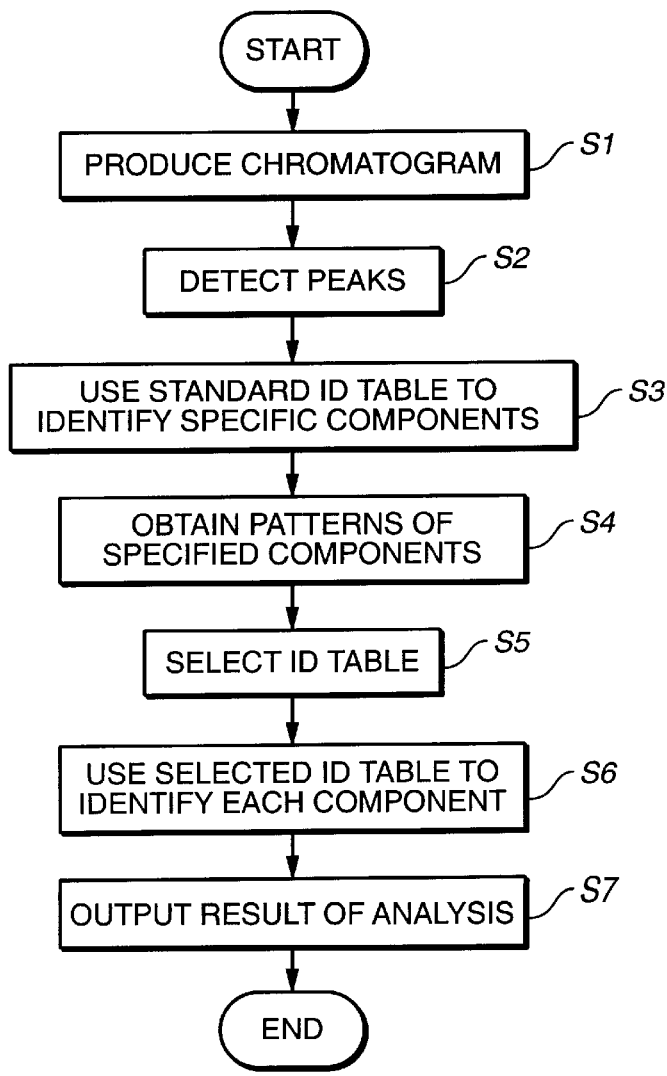
FIG._4

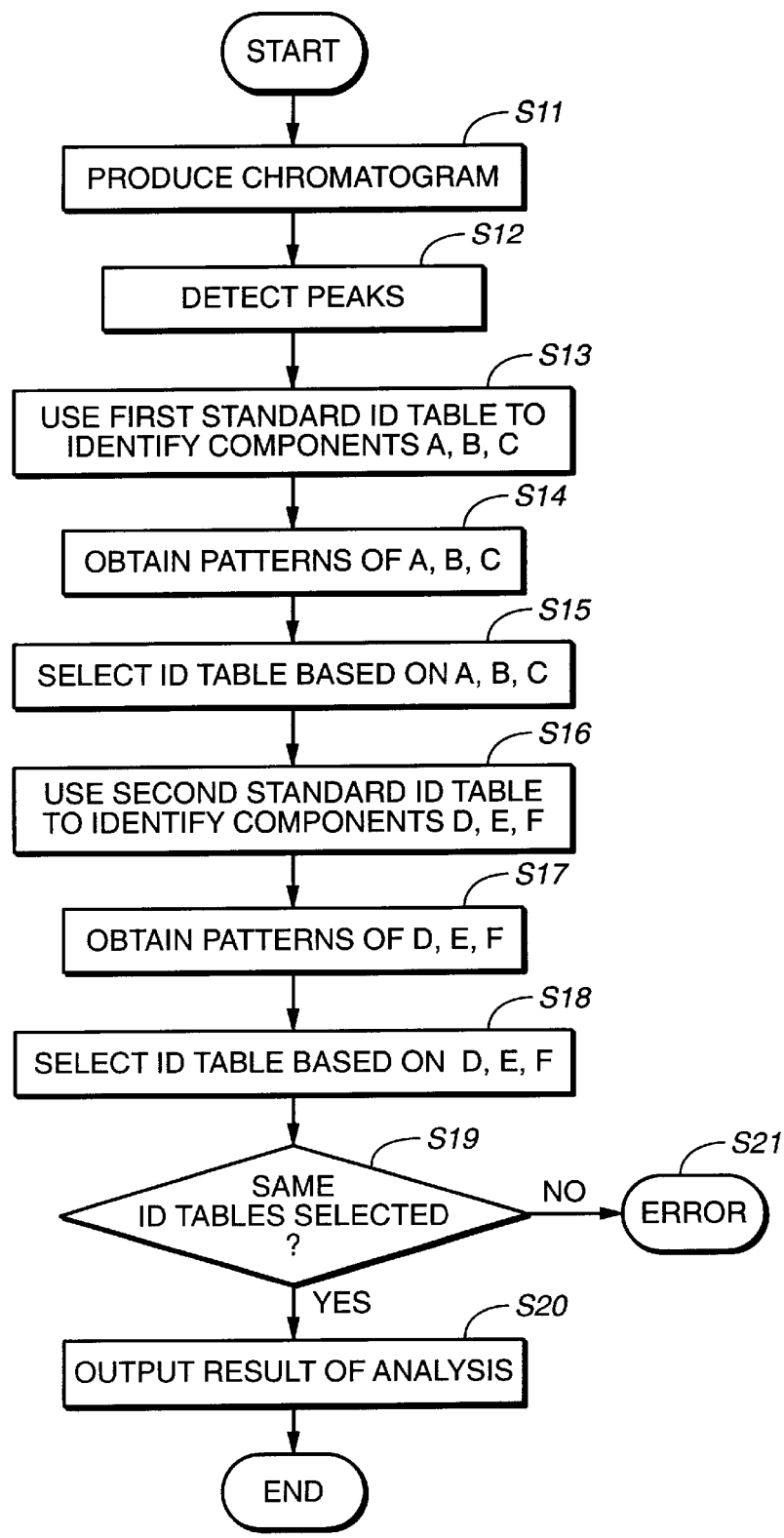
FIG._5

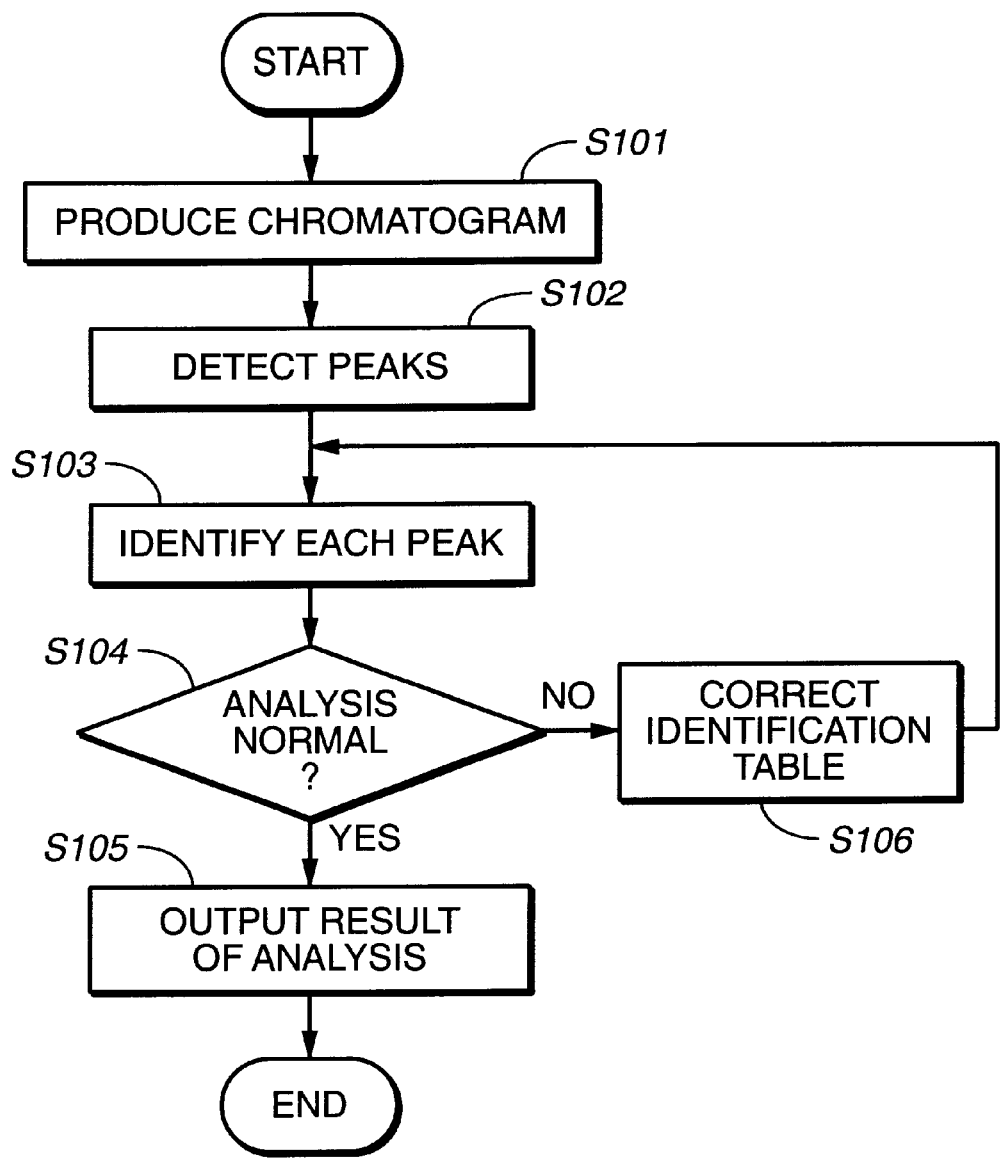
FIG._6
*(PRIOR ART)*

DATA PROCESSING UNIT FOR AND METHOD OF CHROMATOGRAPHY

BACKGROUND OF THE INVENTION

This invention relates to an apparatus for and a method of identifying elements by using specified identification tables to compare data from a chromatogram obtained in gas or liquid chromatography.

FIG. 6 shows steps by which elements contained in a sample are identified in a prior art qualitative analysis. First, an analysis is carried out with a chromatograph to obtain a chromatogram which shows the concentrations of elements (relative intensity) eluted from a separation column as a function of time (Step S101). Peaks are detected by analyzing the chromatogram, from which data such as peak times and peak areas are obtained (Step S102). Next, each of the peak times in the analyzed data is compared with a preliminarily prepared identification table to identify the element corresponding to each peak (Step S103). This identification table is usually prepared by analyzing known materials and contains data such as components, retention times and peak shapes (areas and heights) corresponding to these components. In Step S103, each component is identified by determining the retention time in the table with which each peak time matches.

If the referenced table is inadequate, however, there may remain many unidentifiable components on the chromatogram or components with retention times to which no peak time will match. In such a situation (NO in Step S104), the identification table is either corrected or replaced by another (Step S106) and the step of peak identification (Step S103) is repeated. Only after it is concluded that a normal analysis has been done (YES in Step S104), the results such as the names of the identified components are outputted (Step S105).

By this prior art routine, Steps S103, S104 and S106 must be repeated as many times as necessary until an appropriate identification table can be set. In the analysis of a substance such as gasoline, containing hundreds of different components, each of which may be of different kinds, depending on the supplier, for example, it is extremely difficult to select an appropriate identification table. If it is necessary for the analyzer himself or herself to keep replacing the identification table and repeating the analyses, the qualitative analysis becomes both time consuming and labor consuming.

SUMMARY OF THE INVENTION

It is therefore an object of this invention to eliminate, or substantially reduce the number of unidentifiable components in a qualitative analysis based a chromatogram.

It is another object of this invention to provide an improved technology of qualitative analysis by automatically selecting an identification table for identifying peaks according to the sample.

The technology (apparatus and method) embodying this invention, with which the above and other objects can be accomplished, may be characterized as comprising means for or steps of storing identification tables with different contents corresponding to presences and absences of specified components, identifying peaks corresponding to these specified components in a chromatogram and thereby determining presences and absences of these specified components in the sample, selecting a specified one of the stored identification tables according to the result of the identification, and identifying components corresponding to each of the peaks in the chromatogram by comparing with the selected identification table.

According to this invention, one or more specified components are selected according to the kind of sample to be analyzed, and identification tables with different contents depending on whether or not these selected components are contained are produced and stored in a memory means. Components which can characterize the samples to be analyzed are selected as the specified components. In other words, components of the kind which are contained in each sample by about the same amount are not effective, but those with contents which vary significantly from one sample to another are preferred. Identification tables are produced such that it will be possible to identify all specified components contained in each of samples, which can be distinguished by the presence or absence of these specified components.

When a sample is chromatographically analyzed, presence and absence of specified components are determined by comparing peaks in a chromatogram with an identification table for these specified components. Depending on the result of this determination of presences and absences, a suitable one of identification tables stored in the memory means is selected, and these specified components are identified by comparing each peak in the chromatogram with the values in the selected identification table.

If the selected specified components are such that each sample is to be identified by the magnitudes of their contents (instead of their presence and absence), it is preferable to conclude in the case of a peak which seems to indicate only a small content that the corresponding component is not contained in the peak.

According to this invention, a most suitable one of a plurality of preliminarily stored identification tables is automatically selected for the identification of each peak. Thus, identification of peaks can be accomplished more reliably, and unidentifiable components can be either totally eliminated or their number can be significantly reduced. As a result, the occurrence of failure in analysis becomes less frequent and the waste in time and labor for repeating analysis can be reduced, that is, qualitative analyses can be carried out with a higher efficiency.

BRIEF DESCRIPTION OF THE DRAWINGS

The accompanying drawings, which are incorporated in and form a part of this specification, illustrate an embodiments of the invention and, together with the description, serve to explain the principles of the invention. In the drawings:

FIG. 1 is a block diagram of a gas chromatograph provided with a data processing unit of this invention;

FIG. 2 is a functional block diagram of the data processing unit of FIG. 1;

FIG. 3 is a portion of an identification table;

FIG. 4 is a flow chart of operations embodying this invention by the data processing unit;

FIG. 5 is a flow chart of another mode of operations embodying this invention by the data processing unit; and FIG. 6 is a flow chart of a prior art method of chromatographic qualitative analysis.

DETAILED DESCRIPTION OF THE INVENTION

A data processing unit embodying this invention will be described with reference to FIGS. 1–4. FIG. 1 shows the whole of a gas chromatograph 10 using a data processing unit according to this invention, including a source of carrier gas 11 serving as the mobile phase, a sample vaporization chamber 12, an automatic sample injector 13 for automatically injecting a sample into the sample vaporization chamber 12, a capillary column 14, a detector 15 disposed at the outlet of the capillary column 14, a data processing unit 16 for analyzing detection signals Sd from the detector 15 and a printer 17 for outputting the results of analysis. A personal computer is usually used as the data processing unit 16, and software of different kinds is used with this personal computer to carry out data processing as will be described below.

A chromatographic analysis is carried out first by establishing a flow of carrier gas at a specified rate from the source 11 through the sample vaporization chamber 12 into the capillary column 14. If a liquid sample is instantaneously injected from the automatic injector 13 to the sample vaporization chamber 12, the sample which is vaporized inside the sample vaporization chamber 12 is carried by the carrier gas into the capillary column 14. Each component of the sample is separated time-wise while passing through the column 14 and eluted out with its own retention time. The concentrations of individual components being eluted are sequentially detected by the detector 15 and a detection signal Sd is outputted to the data processing unit 16. The data processing unit 16 serves not only to produce a chromatogram on the basis of the received detection signal Sd but also to analyze this chromatogram, as will be described in detail below, to thereby carry out qualitative and quantitative analyses of the sample.

Operations by the data processing unit 16 are described next with reference to the functional block diagram of FIG. 2 in terms of means for carrying out different processes. Described in this language, the data processing unit 16 includes a chromatogram-producing means 161 for producing a chromatogram on the basis of the detection signal Sd received from the detector 15, a peak-detecting means 162 for detecting peaks from the chromatogram according to a specified standard and obtaining analytical data Sc on each of the detected peaks, a peak-identifying means 163 for identifying components corresponding to each peak by comparing the analytical data Sc with a specified identification table, a memory means 164 for storing a plurality of identification tables as will be described below, and a table-selecting means 165 for selecting an identification table to be used for the identification of peaks.

Each identification (ID) table is structured as schematically shown in FIG. 3, recording for each component contained in samples its retention time and the width of detection window. In the example of FIG. 3, the retention time of Component "a" is 10±1 minutes, that is, in the range of 9–11 minutes. Any number of components may be included in an identification table but since many hundreds of components must be checked in the analysis of gasoline, for example, identification tables containing about one thousand compounds are preferred.

The data processing unit 16 serves to preliminarily select a plurality of components corresponding to the kinds of samples to be analyzed, or a group of samples with similar compositions. In the case of analyzing gasoline samples, for example, it is recognized that there are many different kinds of gasoline of which the main components may be the same but the concentrations of some other components may differ significantly. Thus, such components of which the concentrations differ relatively greatly are selected such that gasoline samples can be more reliably identified (such as in terms of their makers). In the case of gasoline samples, for example, additives such as benzene, toluene and xylene may be favorably treated as specified components.

Next, identification tables are produced, containing all components that are contained in gasoline samples which will be identifiable from the combination of presences and absences of aforementioned plurality of specified components. If three components A, B and C have been specified, for example, there are $2^3=8$ combinations of their presences and absences. Since they are components adapted to characterize the differences among the samples, identification tables which are mutually different and reflect the presences and absences of these specified components corresponding to each of these combinations are produced. Let "1" and "0" respectively indicate presence and absence of each of the three components. Then, the eight identification tables corresponding to the aforementioned eight patterns of presences and absences may be represented as follows:

(A, B, C)=(0,0,0): Identification table No. 1 (ID1);
(A, B, C)=(0,0,1): Identification table No. 2 (ID2);
(A, B, C)=(0,1,0): Identification table No. 3 (ID3);
(A, B, C)=(0,1,1): Identification table No. 4 (ID4);
(A, B, C)=(1,0,0): Identification table No. 5 (ID5);
(A, B, C)=(1,0,1): Identification table No. 6 (ID6);
(A, B, C)=(1,1,0): Identification table No. 7 (ID7);
(A, B, C)=(1,1,1): Identification table No. 8 (ID8);

and eight kinds of such tables are stored in the memory means 164. Aside from these, a standard identification table IDS is produced for the identification of these specified components A, B and C and stored also in the memory means 164. The standard identification table IDS includes only the specified components, their retention times and the widths of their detection windows.

Actual operations by the data processing unit 16, after the plurality of identification tables have been stored in its memory means 164, will be explained next with reference to the flow chart of FIG. 4.

First, the chromatogram-producing means 161 produces a chromatogram after the chromatographic analysis of a given sample is completed (Step S1). On the basis of the data represented by the chromatogram, the peak-detecting means 162 detects the peaks identifiable on the chromatogram (Step S2), for example, by identifying the beginning of a peak where the slope of the curve on the chromatogram exceeds a certain threshold value and the end of the peak where, after the slope becomes zero and then negative, its absolute value exceeds another threshold value. The point where the slope becomes zero may be identified as the peak top. The peak-detecting means 162 identifies the times at which peaks appear (peak times), the heights of the peaks and the areas of the peaks and transmits these analytical data Sc to the peak-identifying means 163.

The peak-identifying means 163 first compares each of the peak times contained in the analytical data Sc with the standard identification table IDS stored in the memory means 164 to identify the three specified components A, B and C (Step S3). In other words, it is checked whether or not each of the inputted peak times corresponds to the retention times in the standard identification table IDS and thereby determined whether the three specified components are present or absent. A pattern (A, B, C) is thus obtained (Step S4).

In aforementioned Step S3 for identifying the specified component, it may be preferable in some situations to increase the threshold values for their identification such that, if a sample contains only very small quantities of a specified component, such a sample will be considered as not containing the specified component. This may be accomplished, for example, by increasing the threshold value of the peak height or the peak area for identifying the presence of a specified component beyond its value when all components are later identified. It is advantageous to thus make flexible the condition for identification of a specified component because the specified components can be selected from a wider range and the effects of noise due, for example, to impurities can be eliminated so as to avoid errors in the identification of the specified components.

The pattern (A, B, C) of the specified components thus obtained is inputted to the table-selecting means 165. The table-selecting means 165 then selects one of the identification tables corresponding to this particular pattern and retrieves it from the memory means 164 (Step S5). The identification table thus selected and retrieved will be hereinafter referred to as "the selected identification table IDX."

Next, the peak-identifying means 163 compares the peak time of each peak contained in the inputted analytical data Sc with the selected identification table IDX and determines which of the retention times in the selected identification table IDX matches with any of the peak times, thereby identifying the components contained in the sample (Step S6). The names and other data of the identified components are outputted through the printer 17 as results of the qualitative analysis (Step S7).

Since the retention times in the identification table are given with a width, as explained above, identifications are possible even if there are some variations in the peak time in the analytical data Sc due to variations in the conditions of analysis or the presence of impurities. In the case of an exceptionally large variation in a condition of analysis, for example, such that unidentifiable components are left which could not be identified by comparing with the selected identification table IDX, a conventional method of correcting the identification table, etc. must be used. Alternatively, as disclosed in Japanese Patent Publication Tokkai 7-239326, the peak times of unidentified components may be displayed on a screen of a display device together with the selected identification table IDS such that the user can operate a mouse or the like while watching such a screen display to input identification data for identifying an unidentified component.

Although the invention has been described above with reference to only one example, this example is not intended to limit the scope of this invention. Many modifications and variations are possible within the scope of this invention. For example, although the identification of specified components in Step S3 is carried out only once according to the embodiment described above before one of the identification tables is selected according to the obtained pattern of the specified components, a more complicated step may be taken for selecting an optimum identification table, as shown, for example, in FIG. 5 by repeating a similar analysis with another set of different components, say, D, E and F.

Explained more in detail, Steps S11 and S12 in the flow chart of FIG. 5 are the same respectively as Steps S1 and S2 of FIG. 4. In Steps S13, S14 and S15, the processes in Steps S4, S5 and S6 are carried out by specifying components A, B and C and using Identification tables Nos. 1–8 (ID1–ID8), as described above. Thereafter, Steps S13, S14 and S15 are repeated as Steps S16, S17 and S18 by specifying different components D, E and F. The components D, E and F are selected such that the $2^3$=8 combinations of their presences and absences will correspond to at least some of the Identification tables Nos 1–8. D, E and F may be selected, for example, such that the eight identification tables corresponding to the aforementioned eight patterns of their presences and absences are as follows:

(D, E, F)=(0,0,0): Identification table No. 2 (ID2);
(D, E, F)=(0,0,1): Identification table No. 1 (ID1);
(D, E, F)=(0,1,0): Identification table No. 4 (ID4);
(D, E, F)=(0,1,1): Identification table No. 3 (ID3);
(D, E, F)=(1,0,0): No Identification table;
(D, E, F)=(1,0,1): Identification table No. 6 (ID6);
(D, E, F)=(1,1,0): Identification table No. 4 (ID4);
(D, E, F)=(1,1,1): Identification table No. 3 (ID3);
where "No Identification table" means that no corresponding identification table is set.

If the same identification table, such as Identification table No. 2 (ID2), was selected in Step S15 on the basis of components A, B and C and in Step S18 on the basis of components D, E and F (YES in Step S19), this identification table is selected as representing the result of the analysis and this result of analysis is outputted (Step S20). If different identification tables are selected in Steps S15 and S18 (NO in Step S19), on the other hand, it is deemed that the identification was not successful or that the analysis ended in an error (Step S21). If (D, E, F)=(1,0,0) is selected in the present example such that there is no corresponding identification table, it is also considered an error. In the case of such an error, another attempt at identification may be made by correcting the conditions for the identification of the components.

In summary, such modifications and variations that are apparent to ordinary persons skilled in the art are intended to be included within the scope of this invention.

What is claimed is:

1. A data processing unit for identifying components in a sample by comparing data obtained from a chromatogram of a chromatographically analyzed sample with specified identification tables, said data processing unit comprising:

plurality of identification tables with different contents, each of said identification tables corresponding to a different combination of presences and absences of a specified set of components;

peak-identifying means for determining whether each of said specified set of components is present or absent from said chromatogram by identifying peaks corresponding to said specified set of components in said sample;

selecting means for selecting one of said identification tables according to the presences and absences of said specified set of components determined by said peak-identifying means; and component-identifying means for identifying components corresponding to each of the peaks in said chromatogram by comparing said each peak with said selected identification table.

2. The data processing unit of claim 1 wherein concentrations of said specified set of components in samples to be analyzed by said unit are significantly different.

3. The data processing unit of claim 1 further comprising a standard identification table containing only data related to said specified set of components for identifying said specified set of components.

4. The data processing unit of claim 3 wherein said standard identification table is stored in a memory means.

5. The data processing unit of claim 3 wherein said standard identification table includes retention times associated with said specified set of components.

6. The data processing unit of claim 5 wherein said peak-identifying means serves to identify said peaks by comparing peak times of said peaks with said retention times in said standard identification table.

7. The data processing unit of claim 3 wherein said peak-identifying means serves to identify said peaks by comparing data on said peaks with the data related to said specified set of components stored in said standard identification table.

8. A method of chromatographically identifying components in a sample, said method comprising the steps of:

obtaining a chromatogram of a chromatographically analyzed sample;

storing a plurality of identification tables with different contents, each of said identification tables corresponding to a different combination of presences and absences of a specified set of components;

identifying peaks corresponding to said specified set of components in said chromatogram and determining for each of said identified peaks presences or absences of said specified components;

selecting a set of said identification tables according to the result of said determined presences and absences; and identifying components corresponding to said each identified peak in said chromatogram by referencing only said selected set of identification tables.

9. The method of claim 8 further comprising the step of selecting said specified components such that concentrations of said specified components in samples to be analyzed by said method are significantly different.

10. The method of claim 9 further comprising the step of producing said identification tables corresponding to said selected specified components.

11. The method of claim 10 wherein each of said identification tables is produced by analyzing samples containing known amounts of said selected specified components.

12. The method of claim 8 further comprising the steps of:

determining for said each identified peak presences and absences of another set of said components;

selecting another set of said identification tables; and identifying components corresponding to said each identified peak by referencing said another selected set of identification tables.

13. The method of claim 12 further comprising the step of determining whether the two steps of identifying components lead to a same result of identification or not.

14. The method of claim 8 further comprising the step of producing a standard identification table containing only data related to said specified components for identifying said specified components.

15. The method of claim 14 further comprising the step of storing said standard identification table together with said plurality of identification tables in a same memory means.

16. The method of claim 14 wherein said standard identification table includes retention times associated with said specified set of components.

17. The method of claim 16 wherein the step of identifying peaks comprises comparing peak times of said peaks with said retention times in said standard identification table.

18. The method of claim 14 wherein the step of identifying peaks comprises comparing data on said peaks with the data related to said specified set of components stored in said standard identification table.

\* \* \* \* \*